United States Patent [19]
Prince et al.

[11] Patent Number: 5,665,542
[45] Date of Patent: *Sep. 9, 1997

[54] *TOXOPLASMA GONDII* P28 GENE AND METHODS FOR ITS USE

[75] Inventors: Jeffrey B. Prince, Mountain View; Fausto G. De Araujo, Palo Alto; Somesh D. Sharma, Los Altos; Jack S. Remington, Menlo Park, all of Calif.

[73] Assignee: Research Institute of Palo Alto Medical Foundation, Palo Alto, Calif.

[*] Notice: The term of this patent shall not extend beyond the expiration date of Pat. No. 5,633,139.

[21] Appl. No.: 264,951

[22] Filed: Feb. 3, 1992

Related U.S. Application Data

[63] Continuation of Ser. No. 431,578, Nov. 3, 1989, abandoned.

[51] Int. Cl.$^6$ ............. C12Q 1/68; C07H 21/02; C07H 21/04
[52] U.S. Cl. ............. 435/6; 536/23.1; 536/24.3
[58] Field of Search ............. 435/6; 530/350; 536/23.1

[56] References Cited

U.S. PATENT DOCUMENTS

| | | | |
|---|---|---|---|
| 4,361,649 | 11/1982 | Remington et al. | 435/7 |
| 4,683,195 | 7/1987 | Mullis et al. | 435/6 |
| 5,215,917 | 6/1993 | De Araujo et al. | 435/252.33 |

FOREIGN PATENT DOCUMENTS

| | | | |
|---|---|---|---|
| 2714074 | 6/1995 | France | C12N 15/11 |
| WO8908700 | 9/1989 | WIPO | C12N 1/20 |
| WO9325689 | 12/1993 | WIPO | C12N 15/30 |

OTHER PUBLICATIONS

Handman et al. (1980) *Immunology* 40:579–88.
Sharma et al. (1984) *J. Immunol.* 133:2818–20.
Mercier et al. (1993) *Mol. Biochem. Parasitol.* 58:71–82.
Parmley et al. (1993) *Mol. Biochem. Parasitol.* 57:161–166.
Prince et al. (1989) *Mol. Biochem. Parasitol.* 34:3–13.
Boulanger et al. (1991) *Biol. Cell* 73:89–97.
Sibley et al. (1995) *J. Cell Sci.* 108:1669–1677.
Murray et al. (1993) *Appl. Parasitol.* 34:235–44.
J.S. Remington et al., *Inf. and Immul.* (1972) 6(5):829–834.

*Primary Examiner*—W. Gary Jones
*Assistant Examiner*—Amy Atzel
*Attorney, Agent, or Firm*—Cooley Godward LLP

[57] ABSTRACT

Genetic material encoding the P28 peptide of *Toxoplasma gondii* has been isolated and characterized. This genetic material allows the production of peptides for use in diagnosis or immunization or can itself be directly used in hybridization assays.

22 Claims, No Drawings

TOXOPLASMA GONDII P28 GENE AND METHODS FOR ITS USE

This application is a continuation of U.S. Ser. No. 07/431,578, Nov. 3, 1989, now abandoned.

BACKGROUND OF THE INVENTION

1. Field of the Invention

This invention relates to the field of genetic engineering and more particularly to the identification and preparation of polynucleotide sequences and polypeptides useful for vaccine development and for detection of a toxoplasma infection by hybridization and immunological assays.

2. Description of the Background

Toxoplasmosis is caused by the protozoan parasite *Toxoplasma gondii*. The disease is traditionally associated with the developing fetus in whom it can cause severe neurological problems manifesting as hydrocephaly, mental retardation, or blindness. In healthy adults, the disease is typically mild, producing few if any symptoms.

Recently, the number of toxoplasmosis cases has dramatically increased as a result of an increase in persons who are in some way immunodeficient, such as resulting from post-transplantation therapy, neoplastic disease, or acquired immunodeficiency syndrome (AIDS). In such immunodeficient patients, the parasite can cause encephalitis, a potentially fatal form of the disease.

The current means of diagnosing toxoplasmosis are costly, time consuming, of limited sensitivity, and associated with substantial risks to the patient. Conventional procedures involving serologic techniques are very often not reliable because of severe immune dysfunction in AIDS patients and because of the recurrent nature of the disease. In pregnant women who are first tested for toxoplasmosis during pregnancy, it is critical to differentiate between current and past infection (currently done by comparing IgG and IgM titers over a period of time.

One problem that currently exists is obtaining sufficient quantities of suitable antigens both for the preparation of vaccines and for use as standards in immunological assays. Current techniques for providing antigen require the growth of protozoa in mice and the continual reinfection of new mice. Availability of a genetically engineered polypeptide antigen capable of being used either as a vaccine or an immunological standard would alleviate numerous problems with the current source of antigen.

Furthermore, the methods of treatment for prevention of toxoplasma infection are currently limited. There are no commercial vaccines available for the control of toxoplasmosis. Treatment of the disease is generally initiated and maintained with a drug regimen involving a combination of pyrimethamine and sulfadiazine. However, toxicity due to the drug treatment can be significant so that prophylactic drug therapy is not recommended except where cysts have actually been detected.

Accordingly, there remains a need for the development of diagnostic assays that reliably detect low levels of toxoplasma infection and of materials useful for the production of vaccines.

SUMMARY OF THE INVENTION

The present invention provides genetic material encoding an antigen of *T. gondii*, specifically that antigen known as P28. The genetic material can be used to produce polypeptides or proteins for use as vaccines or diagnostic reagents, or can be used as a source of probes that can be used in nucleic acid hybridization assays for the direct detection of toxoplasma infections. Specific genetic material and analytical techniques are disclosed in the following detailed description and the examples that follow.

DESCRIPTION OF SPECIFIC EMBODIMENTS

The present inventors have identified and obtained for the first time genetic material encoding the P28 antigen of the protozoan parasite *Toxoplasma gondii*. The P28 antigen, is a major subsurface antigen [see Sibley and Sharma, *Infect. Immunol.* (1987) 55: 2137–2214] and can be used for the production of vaccines or diagnostic standards (the latter for use, e.g., in immunoassays for detecting *T. gondii*). Accordingly, identification and isolation of this specified genetic material allows production of various biochemical components, such as antigens, diagnostic nucleic acid probes, and systems for producing the same, which find a variety of useful biological applications.

Since there is a known and definite correspondence between amino acids in a peptide and the nucleic acid sequence that codes for the peptide, the nucleic acid sequence of a DNA or RNA molecule coding for natural *T. gondii* proteins (or any of the modified peptides later discussed) will readily be understood as indicating particular amino acid sequences, and such exemplary sequences of nucleotides and amino acids are shown in Table 1.

TABLE 1

Nucleotide sequence of one strand of DNA encoding *T. gondii* protein P28 and the sequence of corresponding peptide. The DNA sequence is numbered beginning at the 5' terminus of a cloned sequence that contains the coding sequence. The amino acid sequence of P28 is numbered beginning with the apparent initiation methionine as 1.

P28 Sequence
cDNA Sequence Including Intron (coding sequence underlined)

| | | | | | |
|---|---|---|---|---|---|
| CTGCAGACCA | GATGTCGCAT | TTGAAGGTTA | CATCTCGCTT | GAAGACTTCC | 50 |
| GGTGCCATGT | ATAAGGCAGT | GCCAGCCGCA | TTAGTGCTGT | GTTCGTCGCT | 100 |
| CTTGAAAAGT | TCTGCGAGAC | CGAAGTCGAT | AATTTTAATC | GGAGAGTGAG | 150 |

TABLE 1-continued

Nucleotide sequence of one strand of DNA encoding *T. gondii* protein P28 and the sequence of corresponding peptide. The DNA sequence is numbered beginning at the 5' terminus of a cloned sequence that contains the coding sequence. The amino acid sequence of P28 is numbered beginning with the apparent initiation methionine as 1.

| Sequence | Position |
|---|---|
| GTGAAGTGTC TTGAAAGAGA ATGTTTTCCG GCTTGAGGTC TCTGAGGCAG | 200 |
| AAACGCGACA TGCAGATGGA ACGGCGAACG CCTTTGAACC CAAACGAATC | 250 |
| GCGAAGCTCC AGTGAACTGG ACAAGCAAAT TTGCAATTCG CGTCGTTATC | 300 |
| GCACGTTGTT TCTCTTCCCA CGAATAGTTG TTTTGATTAG ATATTGCTTC | 350 |
| TTCTCCACAT ATCGCCTCAC AATGTTCGCC GTAAAACATT GTTTGCTGGT | 400 |
| TGTTGCCGTT GGCGCCCTGG TCAACGTCTC GGTGAGGGCT GCCGAGTTTT | 450 |
| CCGGAGTTGT TAACCAGGGA CCAGTCGACG TGCCTTTCAG CGGTAAACCT | 500 |
| CTTGATGAGA GAGCAGTTGG GTAAGTTGGC AAAAGTAATG ATAGAGGCAG | 550 |
| GGGTTGAACG ATAGGCGGCT GCAGATTTGT ATAACACAAC ATGATGTAGC | 600 |
| TGCCACGGTT TTTTTTCGGA GAGTGATGCC GTCTGACTGT TCATCGCACC | 650 |
| CATGGGAGCT AGGGAGGTGC GCTTTCTGTG TGATATGTAT TGTCCTAGTC | 700 |
| CAATTTCCCA CGCACTGTAG TGTCTTGAGA CTCGGTGCCA TGTAGAATTT | 750 |
| TGTGTCTGCC TGCAGAGGAA AAGGTGAACA TACACCACCA CTCCCAGACG | 800 |
| AGAGGCAACA AGAGCCAGAA GAACCGGTTT CCCAACGTGC ATCCAGAGTG | 850 |
| GCAGAACAAC TGTTTCGCAA GTTCTTGAAG TTCGCTGAAA ACGTCGGACA | 900 |
| TCACAGTGAG AAGGCCTTCA AAAAAGCAAA GGTGGTGGCA GAAAAAGGCT | 950 |
| TCACCGCGGC AAAAACGCAC ACGGTTAGGG GTTTCAAGGT GGCCAAAGAA | 1000 |
| GCAGCTGGAA GGGGCATGGT GACCGTTGGC AAGAAACTCG CGAATGTGGA | 1050 |
| GAGTGACAGA AGCACTACGA CAACGCAGGC CCCCGACAGC CCTAATGGCC | 1100 |
| TGGCAGAAAC CGAGGTTCCA GTGGAGCCCC AACAGCGGGC CGCACACGTG | 1150 |
| CCCGTCCCAG ACTTTTCGCA GTAATGTTGA CTACGACGAA AGTGATGCGC | 1200 |
| AGGCTGGAAA GCCGCTGAAG GGAGAAGTCT ACAAAGCCGA TCAGTGAAAA | 1250 |
| ATGTGTGGGG AGGTGGTCTT GTTGCAGGAA TGCAATGGTG TTAAGC | 1296 |

Amino Acid Sequence (252 aa):
(Underlining indicates potential sites of N-glycosylation)

MFSGLRSLRQ KRDMQMERRT PLNPNESRSS SELDKQICNS  40

TABLE 1-continued

Nucleotide sequence of one strand of DNA encoding *T. gondii* protein P28 and the sequence of corresponding peptide. The DNA sequence is numbered beginning at the 5' terminus of a cloned sequence that contains the coding sequence. The amino acid sequence of P28 is numbered beginning with the apparent initiation methionine as 1.

| | | | | |
|---|---|---|---|---|
| RRYRTLFLFP | RIVVLIRYCF | FSTYRLTMFA | VKHCLLVVAV | 80 |
| GALVNVSVRA | AEFSGVVNQG | PVDVPFSGKP | LDERAVGGKG | 120 |
| EHTPPLPDER | QQEPEEPVSQ | RASRVAEQLF | RKFLKFAENV | 160 |
| GHHSEKAFKK | AKVVAEKGFT | AAKTHTVRGF | KVAKEAAGRG | 200 |
| MVTVGKKLAN | VESDRSTTTT | QAPDSPNGLA | ETEVPVEPQQ | 240 |
| RAAHVPVPDF | SQ | | | 252 |

The invention has specifically contemplated each and every possible variation of polynucleotide that could be made by selecting combinations based on the possible codon choices listed in Table 1 and Table 2 (below), and all such variations are to be considered as being specifically disclosed.

Since the DNA sequence of the gene has been identified, it is possible to produce a DNA gene entirely by synthetic chemistry, after which the gene can be inserted into any of the many available DNA vectors using known techniques of recombinant DNA technology. Thus the present invention can be carried out using reagents, plasmids, and microorganisms which are freely available and in the public domain at the time of filing of this patent application.

For example, nucleotide sequences greater than 100 bases long can be readily synthesized on an Applied Biosystems Model 380A DNA Synthesizer as evidenced by commercial advertising of the same (e.g., Genetic Engineering News, November/December 1984, p. 3). Such oligonucleotides can readily be spliced using, among others, the technique of preparing overlapping complementary sequences (e.g, 1–100 of coding strand, 0–50 and 51–150 of complementary strand, 101–200 of coding strand, etc.), followed by hybridizing and ligating the strands. Such techniques are well known and are described in detail in, for example, Davis et al., *Basic Methods in Molecular Biology*, Elsevier Science Publ. Co., Inc., New York (1986).

Furthermore, automated equipment is also available that makes direct synthesis of any of the peptides disclosed herein readily available. In the same issue of Genetic Engineering News mentioned above, a commercially available automated peptide synthesizer having a coupling efficiency exceeding 99% is advertised (page 34). Such equipment provides ready access to the peptides of the invention, either by direct synthesis or by synthesis of a series of fragments that can be coupled using other known techniques.

In addition to the specific polypeptide sequences shown in Table 1, peptide fragments based on these sequences and fragments representing minor variations thereof will have the biological activity of the various peptides. For example, fragments of the P28 peptide sequence can readily be prepared and screened for recognition by immunoglobulins specific for the P28 antigen itself. Peptide synthesizers can be used to prepare small polypeptide fragments (e.g., less than 100 amino acids) or techniques of genetic engineering can be used to prepare larger fragments. A simple screening procedure that will identify suitable polypeptide fragments consists of preparing monoclonal antibodies to the P28 antigen, attaching the antibodies to an affinity column, and capturing peptide fragments that are retained by the bound antibody. Polyclonal antisera can be used instead of monoclonal antibodies if desired. This technique has been demonstrated by the ability of antibodies to identify clones containing segments of the P28 gene, as described in detail in the examples that follow.

The ability to prepare and select appropriate immunologically active fragments from a larger protein is well known in the art and is described in a number of publications, including patents. See, for example, U.S. Pat. No. 4,629,783, which describes the preparation of immunologically active fragments of vital proteins.

One common variation is the preparation of a polypeptide of the invention in the form of a fused polypeptide. Such peptides are typically prepared by using the promoter region of a gene known to be expressed in a host and inserting nucleotides that encode all or a major portion of the amino acid sequence of the invention into the genetic sequence for the host protein. Examples of such fused proteins include β-galactosidase fused proteins.

Another technique for preparing immunologically active peptide fragments is to synthesize a series of amino acids of from 5–100 amino acids in length (or any intervening length, such as 10, 15, or any other multiple of 2, 3, or 5 in this range) and screen for immunological activity using an antiserum (or monoclonal antibody). The fragments would be selected along the entire length of the peptide to optimize cross-reactivity (e.g., a series of peptides 20 amino acids in length and comprising $AA_1$–$AA_{20}$, $AA_5$–$AA_{25}$, $AA_{10}$–$AA_{30}$, etc.). The selected fragment would then correspond to particularly useful corresponding nucleotide sequences that could be used to produce large amounts of the peptide for use as described herein.

In addition, minor variations of the previously mentioned peptides and DNA molecules are also contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid (i.e., a conservative replacement) will not have a major effect on the biological activity of the resulting molecule, especially if the replacement does not involve an amino acid at a binding site or other site of biologic activity. Whether a change results in a functioning peptide can readily be determined by direct analysis for function in an immunization or in a diagnostic test that relies on immunogenic specificity. Examples of this process are described later in detail. Peptides in which more than one replacement has taken place can readily be tested in the same manner. Preferred peptides differ at no more than 12, more preferably no more than 5, amino acids in any contiguous group of 20 amino acids. Standard conservative groups of amino acids are shown in parenthesis using the one-letter amino acid code: non-polar (A,V,L,I,P,M); aromatic (F,T,W); uncharged polar (G,S,T,C,N,Q); acidic (D,E); basic (K,R,H). The aromatic amino acids are sometimes considered to belong to the broader-defined nonpolar (F,W) or uncharged polar (T) groups.

Other DNA molecules that code for such peptides can readily be determined from the list of codons in Table 2 and are likewise contemplated as being equivalent to the DNA sequence of Table 1. In fact, since there is a fixed relationship between DNA codons and amino acids in a peptide, any discussion in this application of a replacement or other change in a peptide is equally applicable to the corresponding DNA sequence or to the DNA molecule, recombinant vector, or transformed microorganism in which the sequence is located (and vice versa).

TABLE 2

| GENETIC CODE | |
|---|---|
| Alanine(Ala, A) | GCA, GCC, GCG, GCT |
| Arginine(Arg, R) | AGA, AGG, CGA, CGC, CGG, CGT |
| Asparagine(Asn, N) | AAC, AAT |
| Aspartic acid(Asp, D) | GAC, GAT |
| Cysteine(Cys, C) | TGC, TGT |
| Glutamine(Gln, Q) | CAA, CAG |
| Glutamic acid(Glu, E) | GAA, GAG |
| Glycine(Gly, G) | GGA, GGC, GGG, GGT |
| Histidine(His, E) | CAC, CAT |
| Isoleucine(Ile, I) | ATA, ATC, ATT |
| Leucine(Leu, L) | CTA, CTC, CTG, CTT, TTA, TTG |
| Lysine(Lys, K) | AAA, AAG |
| Methionine(Met, M) | ATG |
| Phenylalanine(Phe, F) | TTC, TTT |
| Proline(Pro, P) | CCA, CCC, CCG, CCT |
| Serine(Ser, S) | AGC, AGT, TCA, TCC, TCG, TCT |
| Threonine(Thr, T) | ACA, ACC, ACG, ACT |
| Tryptophan(Trp, W) | TGG |
| Tyrosine(Tyr, Y) | TAC, TAT |
| Valine(Val, V) | GTA, GTC, GTG, GTT |
| Termination signal | TAA, TAG, TGA |

Key: Each 3-letter triplet represents a trinucleotide of DNA having a 5' end on the left and a 3' end on the right. The letters stand for the purine or pyrimidine bases forming the nucleotide sequence: A = adenine, G = guanine, C = cytosine, and T = thymine. The RNA code is the same except that U (uracil) replaces T.

In addition to the specific nucleotides listed in Table 1, DNA (or corresponding RNA) molecules of the invention can have additional nucleotides preceeding or following those that are specifically listed. For example, poly A can be added to the 3'-terminal; a short (e.g., fewer than 20 nucleotides) sequence can be added to either terminal to provide a terminal sequence corresponding to a restriction endonuclease site, stop codons can follow the peptide sequence to terminate translation, and the like. Additionally, DNA molecules containing a promoter region or other control region upstream from the gene can be produced. All DNA molecules containing the sequences of the invention will be useful for at least one purpose since all can minimally be fragmented to produce oligonucleotide probes and be used in the isolation or detection of DNA from biological sources.

By "equivalent" is meant, when referring to two nucleotide sequences, that the two nucleotide sequences in question encode the same sequence of amino acids. "Complementary," when referring to two nucleotide sequences, means that the two sequences are capable of hybridizing, preferably with less than 5%, more preferably with no mismatches between opposed nucleotides. The term "substantially" preferably means at least 95% by weight, more preferably at least 99% by weight, and most preferably at least 99.8% by weight. The term "isolated" as used herein refers to peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acrylamide gel) but not obtained either as pure substances or as solutions. The phrase "replaced by" or "replacement" as used herein does not necessarily refer to any action that must take place but to the peptide that exists when an indicated "replacement" amino acid is present in the same position as the amino acid indicated to be present in a different formula (e.g., when leucine instead of valine is present at amino acid 53 of P28).

Salts of any of the peptides described herein will naturally occur when such peptides are present in (or isolated from) aqueous solutions of various pHs. All salts of peptides having the indicated biological activity are considered to be within the scope of the present invention. Examples include alkali, alkaline earth, and other metal salts of carboxylic acid residues, acid addition salts (e.g., HCl) of amino residues, and zwitter ions formed by reactions between carboxylic acid and amino residues within the same molecule.

Peptides of the invention can be prepared for the first time as homogeneous preparations, either by direct synthesis or by using a cloned gene or a fragment thereof as described herein. The P28 peptide was previously enriched by affinity chromatography and/or gel electrophoresis, but the resulting material was not free of all other toxoplasma materials.

Although genes and corresponding proteins can be prepared by the totally synthetic techniques discussed above, in preferred embodiments of the invention genetic information is obtained from natural sources and identified as described herein. The genetic material is first obtained in the form of a gene library, using any of numerous existing techniques. The first of these is to randomly shear genomic DNA and insert this sheared material into expression vectors. If enough recombinants are generated, there is a good probability of having at least one recombinant in the population which is expressing a fusion protein corresponding to the antigen of interest. In practice, for a genome the size of $T.$ $gondii$ (about $7 \times 10^7$ bp), at least $5 \times 10^6$ independent recombinants are needed. This allows for the entire genome to be represented by recombinants where at least one insert will exist with one of its ends falling within any 10-base-pair region. Allowing for only 1 in 6 such insertions being in the correct orientation and reading frame, functional recombinants should exist in such a library with fusions corresponding to every 60 base pairs.

Another strategy for preparing gene libraries is to make complementary DNA (cDNA) copies of the total mRNA population of the parasite and to clone these as recombinant molecules in expression vectors. Other investigations indicated that introns were present within the coding regions of other *T. gondii* genes. Although introns do not preclude use of sheared genomic DNA, they increase the number of recombinants which must be screened and make further analyses substantially complicated. Based on this result, use of a cDNA library to obtain *T. gondii* genes is preferred.

Such a library was generated in the laboratory of the inventors and screened with polyclonal and monoclonal antibodies to obtain the genetic information of the present invention. Upon screening $2 \times 10^5$ recombinant phage plaques with polyclonal antibodies that recognized predominantly P28 and another antigen designated P58, 5 clones expressing antigen were isolated from the library. Those clones have been given identification numbers c28, c48, c55, c72, and c75, as discussed in the examples below. Southern blot analysis of genomic DNA revealed that 4 of these clones encoded portions of the same gene, namely the P28 gene of the present invention. The fifth clone appeared to represent a distinct gene that produces an epitope (possibly from P58) with which the antibody also binds. By screening the cDNA library using fragments of the isolated clones, additional non-expressing clones were obtained. As described in detail in the examples that follow, the complete sequence of the gene encoding the P28 peptide was obtained from the sequences of the clones obtained in this fashion.

Now that this sequence has been determined, it is no longer necessary to go through these steps to obtain the genetic material of the present invention. The polymerase chain reaction (PCR) technique can now be used to isolate genes from natural sources in a simpler and more direct manner. Since *T. gondii* specimens are readily available from sources such as the American Type Culture Collection of Rockville, Md., and since PCR probes can be prepared using the sequences set forth in this specification, it is possible to obtain any desired segment of the sequences set forth herein using the PCR technique and commercially available sources of the *T. gondii* genomic material.

Additional experiments have shown that recombinant fusion proteins produced by the c48 and c55 clones identified above are specifically recognized by sera of patients infected with *T. gondii*. Since the c48 fusion protein contains only the terminal 58 amino acids of the predicted protein sequence, which are also present in the c55 fusion protein, the reactive epitope must reside in that region.

The gene encoding the P28 antigen can be used for the production of full or modified peptides using standard techniques of manipulating and growing unicellular microorganisms. Antigens which are candidates for vaccine development and/or diagnostic reagents will include those recognized by serum from infected patients. Additionally, any of the genetic sequences can be used as probes in hybridization assays.

Although the techniques set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of *T. gondii* protein can be enhanced by including multiple copies of the gene in a transformed host; by selecting a vector known to reproduce in the host, thereby producing large quantities of protein from exogeneous inserted DNA (such as pUC8; ptac12; pIN-III-ompA1, 2, or 3; pOTS; pAS1; or pKK223-3); or by any other known means of enhancing peptide expression.

In all cases, a *T. gondii* protein will be expressed when the DNA sequence is functionally inserted into the vector. By "functionally inserted" is meant in proper reading frame and orientation, as is well understood by those skilled in the art. Typically, a gene will be inserted downstream from a promoter and will be followed by a stop codon, although production as a hybrid protein (possibly followed by cleavage) may be used, if desired.

In addition to the above general procedures which can be used for preparing recombinant DNA molecules and transformed unicellular organisms in accordance with the practices of this invention, other known techniques and modifications thereof can be used in carrying out the practice of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,349,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering.

The implications of the present invention are significant in that useful amounts of *T. gondii* proteins and genetic material of the invention will become available for use in the development of hybridization assays or in any other type of assay utilizing these materials as a reagent for use in diagnosis, immunization, therapeutics, and research. Methods of using genetic material in a hybridization assay are disclosed in U.S. Pat. No. 4,683,202, which is herein incorporated by reference. Transferring the *T. gondii* cDNA which has been isolated to other expression vectors will produce constructs which improve the expression of a *T. gondii* polypeptide in *E. coli* or express the polypeptide in other hosts.

Particularly contemplated is the isolation of genes from these and related organisms that express *T. gondii* protein using oligonucleotide probes based on the principal and variant nucleotide sequences disclosed herein. Such probes can be considerably shorter than the entire sequence but should be at least 10, preferably at least 14, nucleotides in length. Intermediate oligonucleotides from 20 to 500, especially 30 to 200, nucleotides in length provide particularly specific and rapid-acting probes. Longer oligonucleotides are also useful, up to the full length of the gene. Both RNA and DNA probes can be used.

In use, the probes are typically labelled in a detectable manner (e.g., with $^{32}P$, $^{3}H$, biotin, or avidin) and are incubated with single-stranded DNA or RNA from the organism in which a gene is being sought. Hybridization is detected by means of the label after single-stranded and double-stranded (hybridized) DNA (or DNA/RNA) have been separated (typically using nitrocellulose paper). Hybridization techniques suitable for use with oligonucleotides are well known.

Although probes are normally used with a detectable label that allows easy identification, unlabeled oligonucleotides are also useful, both as precursors of labeled probes and for use in methods that provide for direct detection of double-stranded DNA (or DNA/RNA). Accordingly, the term "oligonucleotide probe" refers to both labeled and unlabeled forms.

In addition to those uses previously enumerated, proteins produced using the genetic information set forth above have numerous uses in diagnosis and prophylaxis. For example, peptides and peptide fragments can be used in enzyme-linked immunosorbent assays (ELISA) for detection of IgG, IgM, IgA, and IgE antibodies to *T. gondii* in human sera. Antigens of the invention can also be used in the HS/AC agglutination assay described in Thulliez et al., *Path. Biol.*, 34: 173-177 (1986) for the detection of agglutinating antibodies in human sera. Additionally, competitive antibody enzyme immunoassays (CEIA) can be used to detect antibodies in human sera that compete with monoclonal antibodies directed against the P28 antigen. Peptides and peptide fragments of the invention can also be used for the production of monospecific polyclonal antibodies for use in an antigenemia test to detect circulating antigen in patient samples, as described in Araujo et al., *J. Infect. Dis.*, 141: 144-150 (1980).

Additionally, it is possible to determine efficacy of any antigenic peptides or peptide fragments of the present invention for use as a vaccine. The peptide is used to immunize mice either alone, conjugated with purified protein derivative (PPD), incorporated into liposomes or incorporated with Quil A into an immunostimulating complex (ISCOM), or combined with an adjuvant (Freund's complete adjuvant, Freund's incomplete adjuvant, saponin, muramyl dipeptide, interferon-λ, or other adjuvants that might be developed). Immunization will be by the oral route or by multiple injections intraperitoneally or subcutaneously, following which the serological response, delayed-type hypersensitivity (DTH), and cell-mediated immune response will be measured using standard techniques. The immunized mice will be challenged with tachyzoites or cysts of virulent and avirulent strains of *T. gondii*, and the animals will be examined at various times until death for the development of *T. gondii* cysts in the brain and in the skeletal and heart muscle.

It is already known that certain fragments of the P28 peptide have specific use in addition to being part of the entire antigen. A synthetic peptide derived from amino acid residues 140-152 of P28 has induced at least partial protection against toxoplasma in mice when used in conjection with saponin or Freund's incomplete adjuvant. Another peptide fragment demonstrated to be specifically useful is derived from amino acid residues 221-232. This fragment appears to be useful in diagnosis.

The invention now being generally described, the same will be better understood by reference to the following examples which are provided for purposes of illustration only and are not to be considered limiting of the invention unless so specified.

EXAMPLES

Example 1: Isolation and Characterization of P28 cDNA Clones

An expression library was constructed in the vector λgt11 with cDNA made from poly(A)$^+$ RNA of the RH strain of *T. gondii*. This vector provides for expression of the inserted cDNAs as polypeptides fused to β-galactosidase. The technique used was essentially that of Huynh et al., "Construction and screening cDNA libraries in λgt10 and λgt11" in *DNA Cloning*, Glover, D. M., ed., vol. I, pp. 49-78, IRL Press, Oxford.

Briefly, cDNA was synthesized from 2.2 µg of tachyzoite poly(A)$^+$ RNA template using AMV reverse transcriptase, and the second strand was synthesized with DNA polymerase I Klenow fragment followed by S1 nuclease treatment. The double-stranded cDNA was fractionated by chromatography on Sepharase CL-4B, blunt-ended with DNA polymerase I, methylated with EcoRI methylase, and EcoRI linkers added. Following removal of excess linkers by digestion with EcoRI and chromatography on Sephadex G-150, the cDNA was ligated into the EcoRI site in the lacZ gene of λgt11 and packaged in vitro. The library consisted of 0.6×10$^5$ recombinant phage (colorless-pfu) prior to amplification; the names of clones isolated from this library are prefixed with a "c". Another *T. gondii* cDNA library was constructed in λgt11 using cDNA synthesized from RH strain poly(A)$^+$ RNA by the RNase H method; the names of clones isolated from this second cDNA library are prefixed with "Bc".

After amplification in *E. coli* Y1088, the library was plated on *E. coli* Y1090 and screened according to the methods of Huynh et al. with polyclonal mouse anti-F3G3-Ag diluted 1:50 in Tris-buffered saline (TBS) (50 mM Tris-HCL, pH 8.0, 150 mM NaCl) containing 5% nonfat dry milk (Carnation). Bound antibody was visualized by reaction with HRPO-conjugated goat anti-mouse IgG diluted 1:250 to 1:500 in TBS, 0.05% Tween-20. As previously reported in Sibley and Sharma, *Infect. Immunol.*, 55: 2137-2141 (1987), the polyclonal mouse anti-F3G3-Ag used for library screening reacted on immunoblots of reduced *T. gondii* lysate solely with the two components of the F3G3-Ag with apparent molecular masses of 28 and 58 kDa. Upon screening 2×10$^5$ recombinant phage plaques, five clones expressing antigen were isolated from the library. Southern blot analysis of genomic DNA revealed that four of these clones (including c28, c48 and c55) encoded parts of the same gene, while the fifth clone encoded part of a second, distinct gene. The former clones encode the 28 kDa component of the F3G3-Ag; the latter clone may encode the 58 kDa component. By screening the cDNA library on *E. coli* Y1088 using the radiolabeled (by nick translation) EcoRI insert from c28 as a hybridization probe, two non-expressing clones (c72 and c75) were also obtained. Using the EcoRI insert from c48 as a probe, additional clones (including Bc7) were isolated from a second *T. gondii* cDNA library of similar construction (see above). Table 3 summarizes the clones discussed in this example.

TABLE 3 cDNA Clones Encoding the P28 Antigen

| λgt11 Clone | Isolation Method | cDNA Insert Sequence[a] |
|---|---|---|
| c28 | Expression[b] | 410–520/766–1119 |
| c48 | Expression[b] | (1296–997)$_c$352–520/766–881 |
| c55 | Expression[b] | 958–1275 |
| c72 | c28 Hybridization[c] | (1154–1058)$_c$352–1221 |
| c75 | c28 Hybridization[c] | 280–520/766–937 |
| Bc7(PS)[d] | c48 Hybridization[e] | 1–479 |

[a]Numbers correspond to nucleotide positions of the composite P28 cDNA sequence shown in Table 1; ( )$_c$ denotes complement of sequence in parentheses.
[b]Polyclonal mouse anti-F3G3-Ag used as antibody probe.
[c]Clone c28 cDNA insert used as hybridization probe.
[d]PstI/SalI fragment of clone Bc7.
[e]Clone c48 cDNA insert used as hybridization probe.

Example 2: Isolation of *T. gondii* nucleic acids and hybridization with P28 cDNA clones.

The strains of *T. gondii* used were RH (Sabin, JAMA, 16: 801—801 (1941)), C56 (Lycke et al., *J. Bacteriol.*, 96: 785–788 (1968)), M7741 (Remington et al., *J. Immunol.*, 95: 1023–1033 (1966)) and SMH84. The last strain was isolated in our laboratory in 1984 from a brain specimen obtained at autopsy from a patient with AIDS and widely disseminated toxoplasmosis and is maintained in our laboratory by biweekly intraperitoneal passage in female Swiss-Webster mice. These are exemplary strains only, and similar results are expected for other *T. gondii* strains.

For isolation of poly(A)$^+$ RNA for cDNA synthesis, *T. gondii* tachyzoites of the RE strain were harvested 2 days after infection of mouse L929 cells grown to confluency in RPMI 1640 medium (Gibco) containing 10% fetal calf serum at 37° C., under 5% $CO_2$. For isolation of DNA or total RNA for blot analyses, tachyzoites of the RE, M7741 and SMH84 strains were grown in and harvested from the peritoneal cavities of mice as previously described in Prince et al., *Mol. Biochem. Parasitol.*, 17: 163–170 (1985).

Total RNA was isolated from *T. gondii* tachyzoites by the guanidinium thiocyanate extraction method, and poly(A)$^+$ RNA was selected by passage over oligo(dT)-cellulose. Tachyzoite DNA was isolated by lysis with sodium dodecyl sulfate (SDS) and proteinase K, as described by Davis et al., *Basic Methods in Molecular Biology*, Elsevier Science Publ. Co., Inc., New York (1986).

When genomic DNA of the RH strain of *T. gondii* was digested with restriction enzymes that do not cut within the c28 EcoRI insert and was then probed with radiolabeled c28 insert, the probe hybridized with single bands for all enzymes tested except one. The sole exception was PstI, which yielded two bands of approximately 1.3 and 1.0 kb. As discussed below, the c28 cDNA sequence is comprised of parts of two exons that span an intron containing PstI sites. These results therefore indicate that the gene exists as a single copy in the tachyzoite haploid genome. Indentical patterns were obtained with digests of DNA from two additional strains of *T. gondii*, M7741 and SMH84. When total RNA from RE tachyzoites was probed with radiolabeled c48 insert, the probe hybridized with a single major species of 1.1 kb. Upon longer exposure of the autoradiogram, three faint bands at 1.4, 0.9 and 0.6 kb could also be discerned. The same pattern was observed when total RNA was probed with the 1.7 kb EcoRI insert from clone Bc7.

Example 3: DNA Sequencing of Cloned P28 Gene Fragments

Sequencing in M13, mp18 or mp19 was performed by the dideoxy chain terminator method using [$^{35}$S]dATP and Klenow DNA polymerase, or Sequenase™ DNA polymerase. For sequencing in λgt11, template/primer hybrids were prepared by the method of Chen and Seeburg, DNA, 4: 165–170 (1985).

The complete nucleotide sequences of the cDNAs from clones c28, c48, c55, c72 and c75, and a 0.5 kb PstI/SalI fragment of the Bc7 insert, were determined. All of these cDNAs contain portions of a 762-bp open reading frame (ORF). In addition, restriction analysis and direct sequencing in λgt11 were used to determine the orientation of the inserts with respect to the lacZ gene in the expressing clones. The correctly oriented ORF sequences in the c28, c55, and c48 clones are in frame with the β-galactosidase sequence and therefore are expressed as fusion polypeptides. Clone c48 also contains ORF sequence in the reverse orientation adjacent to the β-galactosidase (see below) which nonetheless maintains the correct reading frame and contains no stop codons, permitting readthrough into the correctly oriented ORF sequence.

The cDNA from clone c72 contains an apparent 245-bp intron that is absent from the other clones which contain the flanking sequences. The putative exon/intron splice site (G/GTAAGT) and intron/exon splice site (CCTGCAG/A) are consistent with the consensus sequences derived from the five introns in the α- and β-tubulin genes of *T. gondii*. Presumably, the presence of an intron in the c72 cDNA sequence indicates that incompletely processed nuclear RNA was present in the poly(A)$^+$ RNA used as a template for cDNA synthesis. Indeed a faint band of about 1.4 kb seen in the Northern blots may represent partially processed poly(A)$^+$ RNA containing the intron.

Clone c72 cDNA contains a long, perfect inverted repeat, and clone c48 cDNA contains a larger inverted sequence (apparently derived from an inverted repeat) which is present in the correct orientation in c55. Due to the reverse orientation of the cDNA insert in c48, the ORF within the inverted repeat-derived sequence is expressed as part of the fusion protein in that clone. These long inverted repeats initiate at the site of a heptanucleotide sequence (AGAAGCA) that is directly repeated in the 3' half of the ORF and inversely repeated in the 5' half of the ORF.

Example 4: Composite cDNA and Deduced Amino Acid Sequences of P28

Including the intron in c72, the six clones described in Table 3 together encompass 1296 bp of cDNA sequence. The composite cDNA sequence is presented in Table 1.

Table 1 also shows the deduced amino acid sequence of the largest possible polypeptide initiating with methionine encoded by the ORF. The molecular weight of the putative polypeptide is 28003, in the range expected for the P28 antigen. As indicated in Table 1, there are two potential sites of N-linked glycosylation within the proposed sequence. The polypeptide contains no apparent signal or glycolipid anchor sequence.

Example 5: Antigencity of recombinant P28 Fusion Proteins

To examine the recombinant β-galactosidase fusion proteins synthesized by the three clones isolated with antibody probes, lysogens were prepared in *E. coli* Y1089 and the cell lysates (prepared according to Huynh et al., op. cit.) analyzed by SDS-PAGE.

SDS-PAGE was performed according to the method of Laemmli, *Nature*, 227: 680–685 (1970). Molecular weight markers were Diversified Biotech mid range-prestained: phosphorylase b (94400), glutamate dehydrogenase (55000), ovalbumin (43000), lactate dehydrogenase (36000), carbonic anhydrase (29000), lactoglobulin (18400), cytochrome c (12400); BioRad high molecular weight: myosin (200000), β-galactosidase (116250), phosphorylase b (97400), bovine serum albumin (66200), ovalbumin (42699), carbonic anhydrase (31000), soybean trypsin inhibitor (21500), lysozyme (14400). After separation by SDS-PAGE, proteins were electrophoretically transferred to nitrocellulose paper and reacted with antibody according to the immunoblotting technique of Towbin et al., *Proc. Natl. Acad. Sci. USA*, 76: 4350–4354 (1979). Human sera were from individuals with acute (2 persons) or chronic (2 persons) infection or with no serologic evidence of *T. gondii* infection as assayed by the Sabin-Feldman dye test (DT) and double-sandwich IgM enzyme-linked immunosorbent assay (DS-IgM-ELISA). Sera of humans infected with *T. gondii* employed for immunoblotting had DT titers ranging from 1:1024 to 1:8000 (negative <1:16) and DS-IgM-ELISA titers ranging from 0.1 to 13.4 (negative <1.7). Prior to use in immunoblots of lysogen lysates, all sera were preincubated with a wild-type λgt11 lysogen lysate to remove most anti-*E. coli*/λgt11 antibodies.

While the c48 and c55 lysogens produced quantities of fusion protein sufficient to be readily visualized by staining the gels with Coomassie blue, the c28 fusion protein could only be detected following transfer to nitrocellulose and reaction with anti-β-galactosidase antibodies (data not shown). Similar immunoblotting was performed to verify that the recombinant fusion proteins were recognized by anti-Toxoplasma antibodies. Although the polyclonal mouse anti-F3G3-Ag used to isolate the cDNA clones was no longer available for these studies, immunoblots were carried out using a pool of sera of mice chronically infected with C56 strain of *T. gondii*. This shows that ability to detect cross-reactivity is not restricted to a particular antibody preparation. Under conditions which showed no reactivity with β-galactosidase in the lysate of a wild type λgt11 lysogen, the pool of immune mouse sera reacted strongly with the c48 and c55 fusion proteins. No reaction was observed in control blots performed using a pool of sera of uninfected mice.

Further immunoblot analysis revealed that the c48 and c55 fusion proteins also reacted specifically with sera of humans with antibodies to *T. gondii*. Each of the serum samples from patients with chronic or acute *T. gondii* infection, but neither of two pools of sera from seronegative individuals, reacted specifically with the fusion proteins.

Example 6: Immunologic Confirmation of P28 Gene Identity:

To determine the size of the mature parasite antigen encoded by the recombinant clones, c55 fusion protein was employed to affinity purify human antibodies for use in an immunoblot of *T. gondii* lysate. Briefly, crude lysate of the recombinant lysogen was subjected to SDS-PAGE on a 7% acrylamide gel, electrophoretically transferred to nitrocellulose, and a thin, horizontal strip containing the recombinant fusion protein excised and incubated with immune human serum, diluted 1:50 in TBS, 5% nonfat dry milk, 0.05% Tween-20. After washing the strip to remove unbound antibodies, bound antibody was eluted by incubation in 0.2M glycine-HCl, pH 2.5, 0.15M NaCl, 0.05% Tween-20 for 15 minutes at 20° C. The eluate was immediately neutralized to pH 7.4 by addition of Tris base and adjusted to 5% nonfat dry milk, 0.1% NaN$_3$. Additional details on this technique can be found in Hall et al., *Nature*, 311: 379–382 (1984).

Antibodies specifically bound to and then eluted from c55 fusion protein on nitrocellulose paper were used to probe a blot of whole lysate of the RH strain of *T. gondii*. The eluted antibodies reacted with a single band with an apparent molecular mass of 28 kDa. The reactive band is distinct from P30, the major surface antigen of *T. gondii*, which migrated with an apparent molecular mass of 31 to 33 kDa on this blot and whose sequence is different from that presented here. Similar results were obtained using antibodies eluted from the c48 fusion protein by the same methods. In control immunoblot experiments, human antibodies that bound other antigens present in both c55 and wild type λgt11 lysogen lysates failed to react with antigens of *T. gondii* after elution from nitrocellulose strips. These data support the conclusion that the cloned cDNAs encode a 28 kDa antigen of *T. gondii*.

Example 7: Antigenicity and Immunogenicity of Synthetic Peptides Derived from the P28 Antigen Preliminary immunologic studies have been carried out using synthetic peptides based on the deduced amino acid sequence of the P28 protein. For initial experiments, 5 peptides were synthesized that were predicted to contain antigenic domains according to the assignment of hydropathicity values by the method of Kyte and Doolittle in conjunction with secondary structure predictions calculated from the Chou-Fasman algorithm. The 5 synthetic peptides contain the predicted amino acid residues as follows: PEP (38–46), PEP(107–117), PEP(132–139), PEP(140–152), and PEP(221–232). To determine whether the synthetic peptides were recognized by antibodies in sera of humans acutely or chronically infected with *T. gondii*, an ELISA was performed using peptides conjugated to bovine serum albumin via a succinyl linkage. Although there was some variability in the absorbance values obtained from the sera of different individuals (the tests used two seronegative and nine seropositive individuals), the results suggest that PEP (221–232) is specifically recognized by IgG in the sera of infected individuals. This result is consistent with the observation that the c48 fusion protein, which contains amino acid residues 195–252, reacts specifically with IgG in the sera of humans infected with *T. gondii*.

Although these 5 synthetic peptides were selected solely by criteria that predict antigenic domains likely to stimulate antibody production, their capacity to induce protective immunity was also examined. For this purpose, peptides were conjugated to thyroglobulin carrier, mixed with adjuvant, and used to immunize mice. In the initial experiment, mice were given three weekly injections of 50 μg each of thyroglobulin-coupled peptide or succinylated-thyroglobulin control mixed with Freund's incomplete adjuvant. Upon subsequent challenge with lethal or sublethal doses of *T. gondii*, there was a prolongation of time of survival by only those mice immunized with PEP(140–152). At day 11 after challenge with 1×10$^4$ tachyzoites, 100% of mice in the control group had died, whereas 33% of mice immunized with PEP(140–152) still survived. In this preliminary experiment, however, all of the immunized mice eventually died. A second protection study was performed by immunizing a larger group of test animals with PEP (140–152) mixed with saponin as an adjuvant. In general, saponin induces a stronger cell-mediated immune response than does Freund's incomplete adjuvant, yet similarly does not activate macrophages. By day 21 after challenge with 5×10⁴ tachyzoites, 100% of mice in the control group had died: 30% of the immunized mice survived the infection entirely.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An isolated DNA or RNA molecule, which contains a nucleotide coding sequence encoding *Toxoplasma gondii* protein P28 or a complementary DNA or RNA sequence that specifically hybridizes with said *Toxoplasma gondii* protein P28 sequence.

2. The molecule of claim 1, wherein said molecule contains a sequence selected from the group consisting of:
(A)

| | | | | |
|---|---|---|---|---|
| ATGTTTTCCG | GCTTGAGGTC | TCTGAGGCAG | AAACGCGACA | TGCAGATGGA |
| ACGGCGAACG | CCTTTGAACC | CAAACGAATC | GCGAAGCTCC | AGTGAACTGG |
| ACAAGCAAAT | TTGCAATTCG | CGTCGTTATC | GCACGTTGTT | TCTCTTCCCA |
| CGAATAGTTG | TTTTGATTAG | ATATTGCTTC | TTCTCCACAT | ATCGCCTCAC |
| AATGTTCGCC | GTAAAACATT | GTTTGCTGGT | TGTTGCCGTT | GGCGCCCTGG |
| TCAACGTCTC | GGTGAGGGCT | GCCGAGTTTT | CCGGAGTTGT | TAACCAGGGA |
| CCAGTCGACG | TGCCTTTCAG | CGGTAAACCT | CTTGATGAGA | GAGCAGTTGGA |
| GGAAAAGGTC | AACATACACC | ACCACTCCCA | GACGAGAGGC | AACAAGAGCC |
| AGAAGAACCG | GTTTCCCAAC | GTGCATCCAG | AGTGGCAGAA | CAACTGTTTC |
| GCAAGTTCTT | GAAGTTCGCT | GAAAACGTCG | GACATCACAG | TGAGAAGGCC |
| TTCAAAAAAG | CAAAGGTGGT | GGCAGAAAAA | GGCTTCACCG | CGGCAAAAAC |
| GCACACGGTT | AGGGGTTTCA | AGGTGGCCAA | AGAAGCAGCT | GGAAGGGGCA |
| TGGTGACCGT | TGGCAAGAAA | CTCGCGAATG | TGGAGAGTGA | CAGAAGCACT |
| ACGACAACGC | AGGCCCCCGA | CAGCCCTAAT | GGCCTGGCAG | AAACCGAGGT |
| TCCAGTGGAG | CCCCAACAGC | GGGCCGCACA | CGTGCCCGTC | CCAGACTTTT |
| CGCAG. | | | | |

(B) a DNA sequence encoding the same amino acids as the sequence of (A);

(C) an RNA sequence corresponding to the sequence of (A), wherein every T is replaced with U;

(D) an RNA sequence corresponding to the sequence of (B), wherein every T is replaced with U;

(E) a DNA sequence complementary to the sequence of (A) that specifically hybridizes to the sequence of (A);

(F) a DNA sequence complementary to the sequence of (B) that specifically hybridizes to the sequence of (B);

(G) an RNA sequence corresponding to the sequence of (E), wherein every T is replaced with U; and (H) an RNA sequence corresponding to the sequence of (F), wherein every T is replaced with U.

3. The molecule of claim 1, wherein said molecule is DNA.

4. An isolated nucleic acid molecule comprising a sequence selected from the group consisting of the sequences of (A), (B), (C), and (D) of claim 2.

5. The molecule of claim 1, wherein said molecule is RNA.

6. The molecule of claim 1, wherein said sequence is preceded by a functional promoter sequence 5' to said sequence.

7. The molecule of claim 6, wherein at least one copy of said sequence is present in a functioning recombinant DNA or RNA vector.

8. The molecule of claim 6, wherein said sequence is present as part of a sequence encoding a β-galactosidase fusion product.

9. A genetically engineered microorganism, wherein said microorganism contains the vector of claim 7.

10. The microorganism of claim 9, wherein said microorganism is an *E. coli* strain.

11. An isolated polynucleotide, containing at least 10 consecutive nucleotides selected from the group of nucleotide sequences consisting of: (A)

| | | | | |
|---|---|---|---|---|
| CTGCAGACCA | GATGTCGCAT | TTGAAGGTTA | CATCTCGCTT | GAAGACTTCC |
| GGTGCCATGT | ATAAGGCAGT | GCCAGCCGCA | TTAGTGCTGT | GTTCGTCGCT |
| CTTGAAAAGT | TCTGCGAGAC | CGAAGTCGAT | AATTTTAATC | GGAGAGTGAG |
| GTGAAGTGTC | TTGAAAGAGA | ATGTTTTCCG | GCTTGAGGTC | TCTGAGGCAG |
| AAACGCGACA | TGCAGATGGA | ACGGCGAACG | CCTTTGAACC | CAAACGAATC |
| GCGAAGCTCC | AGTGAACTGG | ACAAGCAAAT | TTGCAATTCG | CGTCGTTATC |
| GCACGTTGTT | TCTCTTCCCA | CGAATAGTTG | TTTTGATTAG | ATATTGCTTC |
| TTCTCCACAT | ATCGCCTCAC | AATGTTCGCC | GTAAAACATT | GTTTGCTGGT |
| TGTTGCCGTT | GGCGCCCTGG | TCAACGTCTC | GGTGAGGGCT | GCCGAGTTTT |
| CCGGAGTTGT | TAACCAGGGA | CCAGTCGACG | TGCCTTTCAG | CGGTAAACCT |
| CTTGATGAGA | GAGCAGTTGG | GTAAGTTGGC | AAAAGTAATG | ATAGAGGCAG |
| GGGTTGAACG | ATAGGCGGCT | GCAGATTTGT | ATAACACAAC | ATGATGTAGC |
| TGCCACGGTT | TTTTTTCGGA | GAGTGATGCC | GTCTGACTGT | TCATCGCACC |
| CATGGGAGCT | AGGGAGGTGC | GCTTTCTGTG | TGATATGTAT | TGTCCTAGTC |
| CAATTTCCCA | CGCACTGTAG | TGTCTTGAGA | CTCGGTGCCA | TGTAGAATTT |
| TGTGTCTGCC | TGCAGAGGAA | AAGGTGAACA | TACACCACCA | CTCCCAGACG |
| AGAGGCAACA | AGAGCCAGAA | GAACCGGTTT | CCCAACGTGC | ATCCAGAGTG |
| GCAGAACAAC | TGTTTCGCAA | GTTCTTGAAG | TTCGCTGAAA | ACGTCGGACA |
| TCACAGTGAG | AAGGCCTTCA | AAAAAGCAAA | GGTGGTGGCA | GAAAAAGGCT |
| TCACCGCGGC | AAAAACGCAC | ACGGTTAGGG | GTTTCAAGGT | GGCCAAAGAA |
| GCAGCTGGAA | GGGGCATGGT | GACCGTTGGC | AAGAAACTCG | CGAATGTGGA |
| GAGTGACAGA | AGCACTACGA | CAACGCAGGC | CCCCGACAGC | CCTAATGGCC |
| TGGCAGAAAC | CGAGGTTCCA | GTGGAGCCCC | AACAGCGGGC | CGCACACGTG |
| CCCGTCCCAG | ACTTTTCGCA | GTAATGTTGA | CTACGACGAA | AGTGATGCGC |
| AGGCTGGAAA | GCCGCTGAAG | GGAGAAGTCT | ACAAAGCCGA | TCAGTGAAAA |
| ATGTGTGGGG | AGGTGGTCTT | GTTGCAGGAA | TGCAATGGTG | TTAAGC, |

(B) a DNA sequence encoding the same amino acids as the sequence of (A);

(C) an RNA sequence corresponding to the sequence of (A), wherein every T is replaced with U;

(D) an RNA sequence corresponding to the sequence of (B), wherein every T is replaced with U;

(E) a DNA sequence complementary to the sequence of (A) that specifically hybridizes to the sequence of (A);

(F) a DNA sequence complementary to the sequence of (B) that specifically hybridizes to the sequence of (B);

(G) an RNA sequence corresponding to the sequence of (E), wherein every T is replaced with U; and (H) an RNA sequence corresponding to the sequence of (F), wherein every T is replaced with U.

12. The polynucleotide of claim 11, wherein said polynucleotide is a labeled polynucleotide.

13. The polynucleotide of claim 11, wherein said polynucleotide contains at least 14 consecutive nucleotides.

14. An isolated nucleic acid molecule, wherein said molecule contains a coding sequence selected from the group consisting of: (A)

| | | | | |
|---|---|---|---|---|
| ATGTTTTCCG | GCTTGAGGTC | TCTGAGGCAG | AAACGCGACA | TGCAGATGGA |
| ACGGCGAACG | CCTTTGAACC | CAAACGAATC | GCGAAGCTCC | AGTGAACTGG |
| ACAAGCAAAT | TTGCAATTCG | CGTCGTTATC | GCACGTTGTT | TCTCTTCCCA |
| CGAATAGTTG | TTTTGATTAG | ATATTGCTTC | TTCTCCACAT | ATCGCCTCAC |
| AATGTTCGCC | GTAAAACATT | GTTTGCTGGT | TGTTGCCGTT | GGCGCCCTGG |
| TCAACGTCTC | GGTGAGGGCT | GCCGAGTTTT | CCGGAGTTGT | TAACCAGGGA |
| CCAGTCGACG | TGCCTTTCAG | CGGTAAACCT | CTTGATGAGA | GAGCAGTTGGA |
| GGAAAAGGTG | AACATACACC | ACCACTCCCA | GACGAGAGGC | AACAAGAGCC |
| AGAAGAACCG | GTTTCCCAAC | GTGCATCCAG | AGTGGCAGAA | CAACTGTTTC |
| GCAAGTTCTT | GAAGTTCGCT | GAAAACGTCG | GACATCACAG | TGAGAAGGCC |
| TTCAAAAAAG | CAAAGGTGGT | GGCAGAAAAA | GGCTTCACCG | CGGCAAAAAC |
| GCACACGGTT | AGGGGTTTCA | AGGTGGCCAA | AGAAGCAGCT | GGAAGGGGCA |
| TGGTGACCGT | TGGCAAGAAA | CTCGCGAATG | TGGAGAGTGA | CAGAAGCACT |
| ACGACAACGC | AGGCCCCCGA | CAGCCCTAAT | GGCCTGGCAG | AAACCGAGGT |
| TCCAGTGGAG | CCCCAACAGC | GGGCCGCACA | CGTGCCCGTC | CCAGACTTTT |
| CGCAG | | | | |

(B) an RNA sequence corresponding to the sequence of (A) wherein every I is replaced with U;

(C) a DNA sequence complementary to the sequence of
(A) that specifically hybridizes to the sequence of (A); and (D) an RNA sequence corresponding to the sequence of
(C), wherein every T is replaced with U.

15. An isolated oligonucleotide, containing at least 10 consecutive nucleotides selected from a the group of nucleotide sequences consisting of: (A)

| | | | | |
|---|---|---|---|---|
| ATGTTTTCCG | GCTTGAGGTC | TCTGAGGCAG | AAACGCGACA | TGCAGATGGA |
| ACGGCGAACG | CCTTTGAACC | CAAACGAATC | GCGAAGCTCC | AGTGAACTGG |
| ACAAGCAAAT | TTGCAATTCG | CGTCGTTATC | GCACGTTGTT | TCTCTTCCCA |
| CGAATAGTTG | TTTTGATTAG | ATATTGCTTC | TTCTCCACAT | ATCGCCTCAC |
| AATGTTCGCC | GTAAAACATT | GTTTGCTGGT | TGTTGCCGTT | GGCGCCCTGG |
| TCAACGTCTC | GGTGAGGGCT | GCCGAGTTTT | CCGGAGTTGT | TAACCAGGGA |
| CCAGTCGACG | TGCCTTTCAG | CGGTAAACCT | CTTGATGAGA | GAGCAGTTGGA |
| GGAAAAGGTG | AACATACACC | ACCACTCCCA | GACGAGAGGC | AACAAGAGCC |
| AGAAGAACCG | GTTTCCCAAC | GTGCATCCAG | AGTGGCAGAA | CAACTGTTTC |
| GCAAGTTCTT | GAAGTTCGCT | GAAAACGTCG | GACATCACAG | TGAGAAGGCC |
| TTCAAAAAAG | CAAAGGTGGT | GGCAGAAAAA | GGCTTCACCG | CGGCAAAAAC |
| GCACACGGTT | AGGGGTTTCA | AGGTGGCCAA | AGAAGCAGCT | GGAAGGGGCA |
| TGGTGACCGT | TGGCAAGAAA | CTCGCGAATG | TGGAGAGTGA | CAGAAGCACT |
| ACGACAACGC | AGGCCCCCGA | CAGCCCTAAT | GGCCTGGCAG | AAACCGAGGT |
| TCCAGTGGAG | CCCCAACAGC | GGGCCGCACA | CGTGCCCGTC | CCAGACTTTT |
| CGCAG | | | | |

(B) a DNA sequence encoding the same amino acids as the sequence of (A);

(C) an RNA sequence corresponding to the sequence of (A), wherein every T is replaced with U;

(D) an RNA sequence corresponding to the sequence of (B), wherein every T is replaced with U;

(E) a DNA sequence complementary to the sequence of (A) that specifically hybridizes to the sequence of (A);

(F) a DNA sequence complementary to the sequence of (B) that specifically hybridizes to the sequence of (B);

(G) an RNA sequence corresponding to the sequence of (E), wherein every T is replaced with U; and (H) an RNA sequence corresponding to the sequence of (F), wherein every T is replaced with U.

16. The molecule of claim 1, wherein said molecule is selected from the group of nucleotide sequences consisting of: (A)

| | | | | |
|---|---|---|---|---|
| ATGTTCGCC | GTAAAACATT | GTTTGCTGGT | TGTTGCCGTT | GGCGCCCTGG |
| TCAACGTCTC | GGTGAGGGCT | GCCGAGTTTT | CCGGAGTTGT | TAACCAGGGA |
| CCAGTCGACG | TGCCTTTCAG | CGGTAAACCT | CTTGATGAGA | GAGCAGTTGGA |
| GGAAAAGGTG | AACATACACC | ACCACTCCCA | GACGAGCGGC | AACAAGAGCC |
| AGAAGAACCG | GTTTCCCAAC | GTGCATCCAG | AGTGGCAGAA | CAACTGTTTC |
| GCAAGTTCTT | GAAGTTCGCT | GAAAACGTCG | GACATCACAG | TGAGAAGGCC |
| TTCAAAAAAG | CAAAGGTGGT | GGCAGAAAAA | GGCTTCACCG | CGGCAAAAAC |
| GCACACGGTT | AGGGGTTTCA | AGGTGGCCAA | AGAAGCAGCT | GGAAGGGGCA |
| TGGTGACCGT | TGGCAAGAAA | CTCGCGAATG | TGGAGAGTGA | CAGAAGCACT |
| ACGACAACGC | AGGCCCCCGA | CAGCCCTAAT | GGCCTGGCAG | AAACCGAGGT |
| CCAGTGGAGC | CCCAACAGCG | GGCCGCACAC | GTGCCCGTCC | CAGACTTTTC |
| GCAGTAA, | | | | |

(B) a DNA sequence encoding the same amino acids as the sequence of (A);

(C) an RNA sequence corresponding to the sequence of (A), wherein every T is replaced with U;

(D) an RNA sequence corresponding to the sequence of (B), wherein every T is replaced with U;

(E) a DNA sequence complementary to the sequence of (A) that specifically hybridizes to the sequence of (A);

(F) a DNA sequence complementary to the sequence of (B) that specifically hybridizes to the sequence of (B);

(G) an RNA sequence corresponding to the sequence of (E), wherein every T is replaced with U; and (H) an RNA sequence corresponding to the sequence of (F), wherein every T is replaced with U.

17. The molecule of claim 1, wherein said molecule is selected from the group of nucleotide sequences consisting of: (A)

| | | | | |
|---|---|---|---|---|
| TTCGCC | GTAAAACATT | GTTTGCTGGT | TGTTGCCGTT | GGCGCCCTGG |
| TCAACGTCTC | GGTGAGGGCT | GCCGAGTTTT | CCGGAGTTGT | TAACCAGGGA |
| CCAGTCGACG | TGCCTTTCAG | CGGTAAACCT | CTTGATGAGA | GAGCAGTTGGA |
| GGAAAAGGTG | AACATACACC | ACCACTCCCA | GACGAGAGGC | AACAAGAGCC |
| AGAAGAACCG | GTTTCCCAAC | GTGCATCCAG | AGTGGCAGAA | CAACTGTTTC |
| GCAAGTTCTT | GAAGTTCGCT | GAAAACGTCG | GACATCACAG | TGAGAAGGCC |
| TTCAAAAAAG | CAAAGGTGGT | GGCAGAAAAA | GGCTTCACCG | CGGCAAAAAC |
| GCACACGGTT | AGGGGTTTCA | AGGTGGCCAA | AGAAGCAGCT | GGAAGGGGCA |
| TGGTGACCGT | TGGCAAGAAA | CTCGCGAATG | TGGAGAGTGA | CAGAAGCACT |
| ACGACAACGC | AGGCCCCCGA | CAGCCCTAAT | GGCCTGGCAG | AAACCGAGGT |
| CCAGTGGAGC | CCCAACAGCG | GGCCGCACAC | GTGCCCGTCC | CAGACTTTTC |
| GCAG, | | | | |

(B) a DNA sequence encoding the same amino acids as the sequence of (A);

(C) an RNA sequence corresponding to the sequence of (A), wherein every T is replaced with U;

(D) an RNA sequence corresponding to the sequence of (B), wherein every T is replaced with U;

(E) a DNA sequence complementary to the sequence of (A) that specifically hybridizes to the sequence of (A);

(F) a DNA sequence complementary to the sequence of (B) that specifically hybridizes to the sequence of (B);

(G) an RNA sequence corresponding to the sequence of (E), wherein every T is replaced with U; and (H) an RNA sequence corresponding to the sequence of (F), wherein every T is replaced with U.

18. An isolated polynucleotide, comprising at least 10 consecutive nucleotides selected from the group of nucleotide of sequences consisting of: (A)

| | | | | |
|---|---|---|---|---|
| TTCGCC | GTAAAACATT | GTTTGCTGGT | TGTTGCCGTT | GGCGCCCTGG |
| TCAACGTCTC | GGTGAGGGCT | GCCGAGTTTT | CCGGAGTTGT | TAACCAGGGA |
| CCAGTCGACG | TGCCTTTCAG | CGGTAAACCT | CTTGATGAGA | GAGCAGTTGGA |
| GGAAAAGGTG | AACATACACC | ACCACTCCCA | GACGAGAGGC | AACAAGAGCC |
| AGAAGAACCG | GTTTCCCAAC | GTGCATCCAG | AGTGGCAGAA | CAACTGTTTC |
| GCAAGTTCTT | GAAGTTCGCT | GAAAACGTCG | GACATCACAG | TGAGAAGGCC |
| TTCAAAAAAG | CAAAGGTGGT | GGCAGAAAAA | GGCTTCACCG | CGGCAAAAAC |
| GCACACGGTT | AGGGGTTTCA | AGGTGGCCAA | AGAAGCAGCT | GGAAGGGGCA |
| TGGTGACCGT | TGGCAAGAAA | CTCGCGAATG | TGGAGAGTGA | CAGAAGCACT |
| ACGACAACGC | AGGCCCCCGA | CAGCCCTAAT | GGCCTGGCAG | AAACCGAGGT |
| CCAGTGGAGC | CCCAACAGCG | GGCCGCACAC | GTGCCCGTCC | CAGACTTTTC |
| GCAG, | | | | |

(B) a DNA sequence encoding the same amino acids as the sequence of (A);

(C) an RNA sequence corresponding to the sequence of (A), wherein every T is replaced with U;

(D) an RNA sequence corresponding to the sequence of (B), wherein every T is replaced with U;

(E) a DNA sequence complementary to the sequence of (A) that specifically hybridizes to the sequence of (A);

(F) a DNA sequence complementary to the sequence of (B) that specifically hybridizes to the sequence of (B);

(G) an RNA sequence corresponding to the sequence of (E), wherein every T is replaced with U; and (H) an RNA sequence corresponding to the sequence of (F), wherein every T is replaced with U.

19. An isolated polynucleotide, comprising at least 10 consecutive nucleotides selected from the group of nucleotide sequences consisting of: (A)

| | | | | |
|---|---|---|---|---|
| | | TTCGCC | GTAAAACATT | GTTTGCTGGT |
| TGTTGCCGTT | GGCGCCCTGG | TCAACGTCTC | GGTGAGGGCT | GCCGAGTTTT |
| CCGGAGTTGT | TAACCAGGGA | CCAGTCGACG | TGCCTTTCAG | CGGTAAACCT |
| CTTGATGAGA | GAGCAGTTGG | GTAAGTTGGC | AAAAGTAATG | ATAGAGGCAG |
| GGGTTGAACG | ATAGGCGGCT | GCAGATTTGT | ATAACACAAC | ATGATGTAGC |
| TGCCACGGTT | TTTTTTCGGA | GAGTGATGCC | GTCTGACTGT | TCATCGCACC |
| CATGGGAGCT | AGGGAGGTGC | GCTTTCTGTG | TGATATGTAT | TGTCCTAGTC |
| CAATTTCCCA | CGCACTGTAG | TGTCTTGAGA | CTCGGTGCCA | TGTAGAATTT |
| TGTGTCTGCC | TGCAGAGGAA | AAGGTGAACA | TACACCACCA | CTCCCAGACG |
| AGAGGCAACA | AGAGCCAGAA | GAACCGGTTT | CCCAACGTGC | ATCCAGAGTG |

-continued

```
GCAGAACAAC TGTTTCGCAA GTTCTTGAAG TTCGCTGAAA ACGTCGGACA
TCACAGTGAG AAGGCCTTCA AAAAAGCAAA GGTGGTGGCA GAAAAAGGCT
TCACCGCGGC AAAAACGCAC ACGGTTAGGG GTTTCAAGGT GGCCAAAGAA
GCAGCTGGAA GGGGCATGGT GACCGTTGGC AAGAAACTCG CGAATGTGGA
GAGTGACAGA AGCACTACGA CAACGCAGGC CCCCGACAGC CCTAATGGCC
TGGCAGAAAC CGAGGTTCCA GTGGAGCCCC AACAGCGGGC CGCACACGTG
CCCGTCCCAG ACTTTTCGCA G
```

(B) a DNA sequence encoding the same amino acids as the sequence of (A);

(C) an RNA sequence corresponding to the sequence of (A), wherein every T is replaced with U;

(D) an RNA sequence corresponding to the sequence of (B), wherein every T is replaced with U;

(E) a DNA sequence complementary to the sequence of (A) that specifically hybridizes to the sequence of (A);

(F) a DNA sequence complementary to the sequence of (B) that specifically hybridizes to the sequence of (B);

(G) an RNA sequence corresponding to the sequence of (E), wherein every T is replaced with U; and (H) an RNA sequence corresponding to the sequence of (F), wherein every T is replaced with U.

20. A method of detecting the presence of *T. gondii* in a sample, comprising;

contacting said sample with the polynucleotide of claim 19 under hybridizing conditions, wherein said polynucleotide hybridizes specifically with *T. gondii* P28 sequences, and detecting formation of a duplex comprising said polynucleotide and DNA or RNA present in said sample.

21. A method of detecting the presence of *T. gondii* in a sample, comprising;

contacting said sample with the polynucleotide of claim 18 under hybridizing conditions, wherein said polynucleotide hybridizes specifically with *T. gondii* P28 sequences, and detecting formation of a duplex comprising said polynucleotide and DNA or RNA present in said sample.

22. The method of claim 21, where said method comprises a polymerase chain reaction.

* * * * *